(12) United States Patent
Niazi (10) Patent No.: US 9,701,933 B2
(45) Date of Patent: Jul. 11, 2017

(54) HARVESTING AND PURIFICATION OR PERFUSION YIELDER (HAPPY) DEVICE

(71) Applicant: Sarfaraz K. Niazi, Deerfield, IL (US)

(72) Inventor: Sarfaraz K. Niazi, Deerfield, IL (US)

( * ) Notice: Subject to any disclaimer, the term of this patent is extended or adjusted under 35 U.S.C. 154(b) by 431 days.

(21) Appl. No.: 14/491,651

(22) Filed: Sep. 19, 2014

(65) Prior Publication Data

US 2016/0083685 A1    Mar. 24, 2016

(51) Int. Cl.
| | | |
|---|---|---|
| *C07K 1/22* | (2006.01) | |
| *C12M 1/16* | (2006.01) | |
| *C12M 1/18* | (2006.01) | |
| *B01D 15/20* | (2006.01) | |
| *B01D 15/38* | (2006.01) | |
| *C12M 1/00* | (2006.01) | |
| *C12M 3/00* | (2006.01) | |
| *C12M 1/12* | (2006.01) | |
| *B01D 15/22* | (2006.01) | |

(52) U.S. Cl.
CPC ............ *C12M 23/20* (2013.01); *B01D 15/22* (2013.01); *B01D 15/3804* (2013.01); *C07K 1/22* (2013.01); *C12M 21/14* (2013.01); *C12M 23/44* (2013.01); *C12M 25/16* (2013.01); *C12M 29/04* (2013.01)

(58) Field of Classification Search
CPC ........ B01D 15/10; B01D 15/14; B01D 15/22; B01D 15/26; B01D 15/36; B01D 15/361; B01D 15/362; B01D 15/363; B01D 15/38; B01D 15/3804; B01D 15/3809; B01D 15/3838; B01D 2015/3838; B01D 24/00; B01D 24/002; B01D 24/005; B01D 24/007; B01D 2221/10; B01J 20/22; B01J 20/24; B01J 20/28026; B01J 39/16; B01J 39/18; B01J 41/09; B01J 2220/4812; B01J 2220/4856; B01J 29/04; C12M 23/20; C12M 21/14; C12M 23/44; C12M 25/16; C12M 29/04; C12M 1/00; C12M 1/12; C12M 1/14; C12M 3/06; C12M 3/062; C12M 21/18; C12M 23/04; C12M 23/34; C12M 23/46; C12M 25/00; C12M 25/02; C12M 25/06; C12M 25/18; C12M 25/14; C07K 1/22
USPC ....... 210/261, 262, 264, 266, 283, 290, 291, 210/638, 690, 691, 198.2, 656; 435/288.4, 288.6, 308.1
See application file for complete search history.

(56) References Cited

U.S. PATENT DOCUMENTS

| | | | |
|---|---|---|---|
| 3,463,320 A | 8/1969 | Patterson | |
| 4,935,142 A * | 6/1990 | Sternberg | ............... B01D 29/05 210/321.75 |
| 5,605,835 A | 2/1997 | Hu et al. | |
| 7,785,535 B2 * | 8/2010 | Chen | ....................... B01L 3/502 422/413 |

(Continued)

OTHER PUBLICATIONS

Product Bulletin: Poros Affinity Chromatography Columns, Applied Biosystems by Life Technologies, Life Technologies Corp. 2012.*

(Continued)

*Primary Examiner* — Joseph Drodge
(74) *Attorney, Agent, or Firm* — Sharfaraz K. Niazi (57) ABSTRACT

A modular device comprising one or more porous substrate subunits comprising a binding substrate that is capable of interacting with a target biological product, either during, or at the end of a manufacturing cycle; and methods of using the device to harvest or purify a biological product.

5 Claims, 9 Drawing Sheets

(56) References Cited

U.S. PATENT DOCUMENTS

| | | | |
|---|---|---|---|
| 8,852,435 B2* | 10/2014 | Niazi | B01D 15/22 210/638 |
| 2007/0039891 A1* | 2/2007 | Boschetti | B01D 15/362 210/656 |
| 2009/0179146 A1* | 7/2009 | Lomas | B01L 3/5025 250/282 |
| 2011/0236932 A1 | 9/2011 | Stobbe | |
| 2012/0009667 A1 | 1/2012 | Peterson et al. | |
| 2012/0149021 A1 | 6/2012 | Yung et al. | |
| 2012/0252008 A1 | 10/2012 | Brown et al. | |
| 2012/0289468 A1* | 11/2012 | Barnett | C07K 14/755 514/14.1 |
| 2013/0196375 A1* | 8/2013 | Strobbe | C12M 23/34 435/69.4 |
| 2014/0227769 A1* | 8/2014 | Strobbe | C12M 23/34 435/287.1 |
| 2014/0339170 A1* | 11/2014 | de los Reyes | B01D 15/206 210/656 |

OTHER PUBLICATIONS

Publication: Margit Roobol-Boza et al, "Perfusion Chromatography—a new procedure for very rapid isolation of intergral photosynthetic membrane proteins", Photosynthesis Research, vol. 46, pp. 339-345, 1995.*

International Search Report and Written Opinion for corresponding PCT/US15/51007, dated Feb. 5, 2016.

* cited by examiner

HARVESTING AND PURIFICATION OR PERFUSION YIELDER (HAPPY) DEVICE

BACKGROUND OF THE INVENTION

Currently over 100 biological products are produced using recombinant technology wherein bacterial or mammalian DNA is modified to direct host cells to express and/or secrete proteins of interest. In the future, it is anticipated that more than three-fourth of all new drugs will be biologics, including drugs expressed using recombinant host cells cultured in bioreactors.

When using host mammalian cells, which represents the most significant cell used in recombinant drug expression for the manufacturing process, the standard upstream unit operations involves culturing recombinant host cells in a bioreactor under conditions which promote the expression and secretion of the target biological proteins into the culture media.

The current trend for cell culture processes is to increase product titer through using enriched culture media, or longer periods of culture duration. However, the increased cell mass and improved cell productivity, is usually accompanied by decreased levels of cell viability, and an increased likelihood that the target biologic will be exposed to unfavorable environmental conditions attributed to increased levels of process impurities (e.g. such as host cell proteins, nucleic acids, lipids, colloids) present in the cell culture media.

Typically, the first upstream unit operations involve separating the mammalian cells from the culture media at the end of the cycle (e.g., by centrifugation, precipitation and/or filtration) and reducing the media volume by ultrafiltration in order to prepare the biological protein for subsequent downstream processing using a series of unit operations designed to purify the target protein from undesirable culture by-products, host cell proteins and process related impurities or contaminants.

It has been estimated that downstream processing accounts for 50% to 80% of the total manufacturing cost of a therapeutic antibody. The purification unit operations of a typical protein manufacturing process routinely involve a capture step and at least one, and typically more than one, polishing step. It is well known that the standard unit operations used to manufacture biological products are characterized by disadvantages resulting from the use of cell separation techniques that require the use of high G-force centrifugation, or shear forces that can negatively impact host cell integrity, as well as the quality of the biological product.

For example, the use of an ultrafiltration step to concentrate the drug substance at the end of the upstream unit operations can result in lower yields or poor quality product that is more likely to exhibit inconsistency in its structure. Additionally, the cost of equipment, the long process times and the validation of cleaning required for GMP manufacturing can make the traditional process extremely cumbersome, inefficient and expensive.

In addition to the concerns discussed above, there can also be issues with the effect of spent cell culture media on the viability of the host cell and/or the quality of the expressed biological target protein. Many metabolites and by-products (e.g., host cell proteases) released during high cellular density culture conditions can be detrimental to the stability and quality of a targeted biological product. Some of these concerns can be minimized by using a perfusion-based culture system in which the culture media is constantly refreshed by the addition of fresh culture media, the high cost of cell culture media (ranging from less than $5/L for bacterial culture to over $100/L for mammalian culture) makes this option extremely expensive. In addition, depending on the scale of the manufacturing operation, perfusion or fed batch culture methods can be a cumbersome and time consuming process.

Therefore, there is an unmet need for robust manufacturing methods that are streamlined to reduce the cost, and increase the efficiency of processes used to manufacture biological products. Ideally, an optimized manufacturing process should reduce the level of stress the target biologic product is exposed to, improve the efficiency of the process and reduce the costs by combining or reducing some of the unit operations that are routinely used in established protocols.

SUMMARY OF THE INVENTION

The invention provides a device designed to optimize the standard manufacturing process used to produce biological products and a method for using the disclosed device to streamline the production and purification steps into a more continuous operation. More specifically, the instant invention provides a modular device that allows consolidation of harvesting and purification of target biological products from a culture media. At a minimum, the device and methods of the invention, consolidates three common steps in the manufacturing of target biological products: biological entity removal, volume reduction and harvesting or capture of a target biologic product. The instant invention therefore promises to simultaneously reduce the cost of manufacturing and improve product quality.

The invention provides a harvesting and purification or perfusion yielding (HAPPY) device having a modular design which comprises: a) a top housing subunit and a bottom housing subunit adapted to connect to each other, each of which comprises a port to facilitate the flow of liquid into and out of the device; b) at least one substrate subunit having a top and bottom surface, disposed between the top and bottom subunits, wherein the interior cavity of the substrate subunit is defined by a housing wall and wherein the top and bottom subunits comprise a porous mesh material covering; and c) the interior cavity of the substrate subunit comprises a volume of binding substrate capable of binding a target product.

In an alternative embodiment, the HAPPY device comprises: a) a top housing subunit and a bottom housing subunit adapted to connect to each other, each of which comprises a port to facilitate the flow of liquid into and out of the device; b) a flexible tubular housing defining an interior cavity dimensioned to contain a plurality of substrate subunits disposed between the top and bottom housing subunits; c) at least one substrate subunits comprising a top and a bottom surface that is covered with a porous mesh material and an interior cavity dimensioned to fit snuggly within the tubular housing and comprises a volume of binding substrate; and d) at least one clamp secured to the exterior surface of the tubular housing positioned to secure each substrate subunit to the housing and to prevent liquid from flowing around the substrate subunits.

In some embodiments, the HAPPY devices of the invention comprise a single substrate subunit that is chosen based on the size and/or design of its interior cavity. For example, if the device is being used to remove a metabolic by-product from a bioreactor, it may be desirable to have a single substrate subunit with a large interior cavity suitable to accommodate a granular substrate. Alternatively, if the HAPPY device is being used to perform a downstream unit operation, such as protein purification, it may be more suitable to use a device comprising a single substrate subunit that comprises a plurality of discrete channels that pass through the entire body of the subunit. In practice, the channels can be filled directly with substrate, or the channels can function as holders that are capable of receiving tubes or other containers that have been pre-filled with a substrate. For example, the substrate can comprise a chromatography resin. The presence of multiple channels in the substrate subunit facilitates the use of different combinations of substrates, for example different types of ion exchange resins in a single unit operation.

In order to facilitate the use of HAPPY devices comprising multiple substrate subunits, the device is designed to have a modular design that can be assembled by stacking substrate subunits into discrete stacks or sets of substrate subunits. Each stack or set of substrate subunits can be used either alone or in series to perfuse, harvest, and/or purify a bioreactor cell culture. In practice, the substrate subunit can comprise a solid ring shaped circular object, but it can have any shape, e.g., a square or rectangle. The subunit can comprise, but is not limited to, a plastic material, stainless steel, aluminum or a composite material.

The porous mesh material can comprise, but is not limited to, a flexible material, a hard substance like stainless steel, or a combination of materials. Use of a stainless steel mesh may be particularly useful for substrate subunits that will be used in a flow-path that is incorporated into a perfusion culture system, because it will be more amenable to different methods of sterilization. Depending upon the materials that the different subunits of a particular HAPPY device are made from, it may be necessary to sterilize the housing and connecting tubes of the device separate from the binding substrate. The device can be sterilized by standard techniques, such as radiation or autoclaving.

A myriad of arrangements of HAPPY devices containing a resin that binds the target biological product or metabolic products allows for a modular-designed system that can be customized for specific processes.

In a first embodiment, the invention is a chromatography device used at the end of the bioprocessing upstream cycle to harvest, capture and purify a target biological product.

In a second embodiment, the instant invention is an adsorbent device that removes undesirable metabolites from a bioreactor either continuously or intermittently.

In a third embodiment, the instant invention is a perfusion device that removes the expressed target biological material.

In a fourth embodiment, the instant invention is a perfusion device as well as a device that regenerates the media by removing undesirable metabolic components.

In a fifth embodiment, the instant invention is a purification chromatography device that concentrates a target biological product and removes impurities.

In a sixth embodiment, the instant invention combines multiple chromatography steps in one device. For example, the perfusion device of the instant invention that captures the target biological product can be combined with a second HAPPY device that regenerates the media by removing the undesirable metabolic components. In addition, a third HAPPY device can be incorporated to begin the purification process.

In a seventh embodiment, the instant invention is used to remove a target biological product toxic to the cells.

In an eight embodiment, the instant invention provides a modular chromatography device that can be expanded in size without the need for the revalidation of the device or retesting the efficiency of binding since each module is of the same size and dimension.

In a ninth embodiment, the instant invention provides combining several chromatography steps by allowing use of separate binding substrates, such as resins, in a series.

In a tenth embodiment, the instant invention provides testing of parallel devices to study their efficiency for reducing the development time for the process of purification or perfusion.

In an eleventh embodiment, the instant invention substantially reduces the cost of biological manufacturing by allowing continuous use of the same culture media, use of smaller bioreactors due to perfusion and by eliminating several bioprocessing steps that require substantial capital and functional investment.

In a twelfth embodiment, the instant invention allows very small scale manufacturing and then scaling it up to any size without further need for process step validation since the HAPPY device can be made of any size while providing exactly the same characteristics.

The invention also provides methods of using the HAPPY devices of the instant invention to design a robust production process for the harvesting of a target biological product from a cell culture media (CCM) comprising the steps of: a) making a tubular connection between a bioreactor source of CCM comprising a target product and a port of at least one harvesting, purification or perfusion HAPPY device of the invention thereby creating a flow path; b) forcing the CCM into the flow path and through the substrate subunits of the device either under gravity or by action of a pump; c) maintaining the CCM under conditions that allow binding of the target biological product to the substrate contained within the substrate subunit, thereby harvesting the target product of interest; and optionally, d) collecting the product-depleted CCM flowing out of the outlet port of the device and returning it to the bioreactor or discarding it.

The disclosed HAPPY devices can be used to harvest, perfuse, and/or purify biological target products produced by any recombinant host cell that is amenable to cell culture including mammalian cells, bacteria, yeast, hybridoma cell lines, baculovirus, and plant cells.

As disclosed herein, the HAPPY device of the invention can be placed in a flow path either upon completion of a bioreactor production cycle, intermittently during the production cycle, or continuously during a production cycle in order to capture the target biological product. The eluate from the HAPPY device containing the target product of interest may be further processed using traditional unit operations, or may be diverted into an alternative continuous flow path using HAPPY devices comprising substrates appropriate for in-line purification of the target biologic product.

In an alternative embodiment, HAPPY devices of the instant invention that comprise a substrate that is capable of absorbing and/or neutralizing an undesirable metabolic by-product may be introduced into the flow-path of a bioreactor and used continuously for the duration of a bioreactor production cycle to remove one or more metabolic by-products. Metabolic by-products include, but are not limited to, acetate, carbon dioxide, endotoxins, ethanol, lactic acid, citric acid, glutamic acid, lysine, threonine, tryptophan and other amino acids, antibiotics, antiseptics, bacteriocins, and fungicides. When used in this context, the device will facilitate the use of perfusion-like culture conditions to achieve high cell density cultures with optimized host cell viability and production yields. This use of the HAPPY devices can also be used to minimize the adverse-effect of unfavorable environmental conditions including, but not limited to, conditions, such as decreased pH, that are known to adversely affect not only host cell viability, but also product quality.

DETAILED DESCRIPTION OF THE INVENTION

In order that the present invention may be more readily understood, certain terms are first defined.

As used herein, the term "robust process" or "robust manufacturing process" refers to a process that performs adequately within it operation parameters, consistently providing material of defined quality, purity and yield.

As used herein, the term "cell culture media" or "CCM" refers to a chemically defined medium or undefined media in which recombinant host cells are cultured and into which proteins are secreted, provided that the expression vector introduced into the host cell contains appropriate cellular signals, such as signal peptides.

As used herein, the term "upstream process" refers to process steps associated with the production of a recombinant protein by culture and propagation of host cells. Upstream process considerations include clone selection methodologies, media selection, fed-batch feeding strategies or perfusion culture operating conditions.

As used herein, the term "downstream process" refers to process steps associated with the purification of a recombinant protein and removal of impurities.

The term "metabolic waste product" as used herein refers to a compound produced by the cell culture as a result of normal or non-normal metabolic processes that are in some way detrimental to the cell culture, particularly in relation to the expression or activity of a desired recombinant polypeptide or protein. For example, the metabolic waste products may be detrimental to the growth or viability of the cell culture, may decrease the amount of recombinant polypeptide or protein produced, may alter the folding, stability, glycosylation or other post-translational modifications of the expressed polypeptide or protein, or may be detrimental to the cells and/or expression or activity of the recombinant polypeptide or protein in any number of other ways. Exemplary metabolic waste products include, but not limited to, lactate, produced as a result of glucose metabolism, or ammonium, produced as a result of glutamine metabolism. A cell culture may produce one or more metabolic waste products.

The terms "Chinese hamster ovary cell protein" and "CHOP" are used interchangeably to refer to a mixture of host cell proteins ("HCP") derived from a Chinese hamster ovary ("CHO") cell culture. The HCP or CHOP are generally present as an impurity in a cell culture medium or lysate comprising a target protein of interest, such as a cytokine or a recombinant monoclonal antibody (mAb) admixed with metabolic by-products or process contaminants. The amount of CHOP present in a mixture comprising a protein of interest provides a measure of the degree of purity for the protein of interest. Typically, the amount of CHOP in a protein mixture is expressed in parts per million relative to the amount of the protein of interest in the mixture. It is understood that where the host cell is another cell type, e.g., a eukaryotic cell other than CHO cells, an insect cell, or a plant cell, of a yeast cell, HCP refers to the proteins, other than target protein, found in a lysate of that host cell.

The terms "target protein" and "protein of interest" as used interchangeably herein, refer to a protein or polypeptide, including but not limited to, a cytokine, growth hormone, monoclonal antibody (mAb) or fusion protein that is to be captured purified by a method of the invention, from a mixture of proteins and, optionally, other materials such as cell debris, DNA, host cell proteins, media components, and the like.

The target biological product may comprise any protein, antibody or peptide, either recombinant or synthesized, including but not limited to, a solubilized inclusion body, enamel matrix protein, a fusion protein, a tag protein, a hormone, (such as, thyroid hormone, parathyroid hormone, growth hormone or melanocyte stimulating hormone), gonadotropin, insulin, ACTH, prolactin, placental lactogen, thyrotropin, calcitonin, enkephalin, angiotensin, cytokines, human serum albumin, bovine serum albumin, ovalbumin, glucose isomerase, α-amylase, endo-β, glucanase, growth hormone (GH), IGF-1, IGF-2, PTH, PGE2, TGF-β, TGF-α, bEGF, EGF, PDGF-AB, PDGF-BB, osteoprotegerin (OPG), osteopontin (OP), FGF-1, FGF-2, BMP-2, BMP-3, BMP-4, BMP-6, BMP-7, VEGF, L25(OH)2, vitamin D3, IFN-alpha, IFN-beta, IFN-gamma, OCN (osteocalcin), ON (osteonectin), OP-1 (osteogenic protein-1), NGF, collagen, and clotting factors, such as fibronectin, fibrinogen, thrombin, or factor XIII.

The term "chromatography" refers to any kind of technique that separates an analyte of interest (e.g., a monomer mAb) from other molecules present in a mixture. The term "chromatography resin" or "chromatography media" are used interchangeably herein and refer to any kind of solid phase which separates an analyte of interest (e.g., an Fc region containing protein, such as an immunoglobulin) from other molecules present in a mixture. Non-limiting examples include cation exchange resins, affinity resins, anion exchange resins, anion exchange membranes, hydrophobic interaction resins and ion exchange monoliths. The volume of the resin, as well as the dynamic capacity and flow-rate of the CCM through the HAPPY devices of the invention will depend on several parameters, such as the volume of culture fluid, theoretical yield of the target product that is expected to be produced during the bioreaction cycle, binding capacity of the substrate, and the total number of substrate subunits present in the flow path. Determination of these parameters for each step is well within the skills of the average person skilled in the art.

The terms "Protein A," "ProA," and "PrA" are used interchangeably herein and encompass Protein A recovered from a native source thereof, Protein A produced synthetically (e.g., by peptide synthesis or by recombinant techniques), and variants thereof which retain the ability to bind proteins that have a CH2/CH3 region, such as an Fc region. Protein A is generally immobilized on a solid phase support material. The term "ProA" also refers to an affinity chromatography resin or column containing chromatographic solid support matrix to which Protein A is covalently attached.

As used herein, the terms "ion-exchange" and "ion-exchange chromatography" are used to refer to chromatographic processes in which a target product of interest ("target POI") contained in a solution or mixture interacts with a charged compound linked to a solid phase ion exchange material. The target POI interacts non-specifically with the charged compound either more or less than the impurities or contaminants also present in the solution or mixture. The impurities or contaminates in the mixture elute from the ion exchange material faster or slower than the target POI or are bound to or excluded from the resin relative to the target POI. "Ion-exchange chromatography" includes cation exchange, anion exchange, and mixed mode ion exchange chromatography.

As used herein, the term "mixed-mode chromatography" refers to the use of solid phase chromatographic media that employ multiple chemical mechanisms to adsorb the target POI or other solutes. Examples of mixed mode chromatographic supports include, but are not limited to, chromatographic supports that exploit combinations of two or more of the following mechanisms: anion exchange, cation exchange, hydrophobic interaction, hydrophilic interaction, hydrogen bonding, pi-pi bonding, and metal affinity.

As used herein, the term "harvest" or "capture step" refers to a downstream processing unit operation that captures the target product of interest from the harvested culture media, concentrates the product, and achieves a first separation of the target POI from impurities (e.g., cells, cell debris, DNA, host cell proteins).

The term "affinity separation," or "affinity purification," as used herein, refers to any purification or assay technique that involves the contacting a sample containing a target POI (e.g., an Fc region containing protein) with an affinity media (e.g., a solid support carrying on it an affinity ligand known to bind the target POI, such as, for example, e.g., Protein A, Protein G, or variants thereof) known to bind the target POI.

As used herein, the term "polishing step" refers to a downstream processing step that occurs after the initial capture step and that is intended to remove smaller amounts of impurities that are present in the product stream and that are typically have more similarity to the product (i.e., monomeric antibody) than the impurities removed during the capture step (e.g., aggregated forms of the product, structural variants including misfolded product and modified product).

As used herein the term "binding" is used to describe the interaction between a target protein and a substrate such as a chromatography resin. Binding occurs when the target protein is exposed to or contacted with a chromatography resin under appropriate conditions (pH/ionic strength/conductivity/osmolality) such that the molecule is reversibly immobilized in or on the chromatography resin by virtue of substrate-target protein interactions. Non-limiting examples include ionic interactions between the molecule and a charged group or charged groups of the ion exchange material and a biospecific interaction between Protein A and an immunoglobulin.

The term "specific binding" as used herein, such as to describe interactions between a target protein (e.g., an Fc region containing protein) or a metabolic by-product and a ligand bound to a solid support (e.g., Protein A bound to a solid phase matrix or resin). The term generally refers to a reversible binding of a protein of interest to a ligand through the combined effects of spatial complementarity of protein and ligand structures at a binding site coupled with electrostatic forces, hydrogen bonding, hydrophobic forces, and/or van der Waals forces at the binding site. Generally, the greater the spatial complementarity and the stronger the other forces at the binding site, the greater the binding specificity of a protein for its respective ligand. Non-limiting examples of specific binding include antibody-antigen binding, enzyme-substrate binding, enzyme-cofactor binding, metal ion chelation, DNA binding protein-DNA binding, and the like.

As used herein, the terms "flow-through process," "flow-through mode," and "flow-through chromatography," are used interchangeably herein to refer to a target product separation technique in which at least one product (i.e. target protein) contained in a sample that also contains one or more contaminants is intended to flow through a chromatographic resin or media, while at least one potential contaminant or impurity binds to the chromatographic resin or media. The "flow-through mode" is generally an isocratic operation (i.e., a chromatography process during which the composition of the mobile phase is not changed).

As used herein, the term "buffer exchange step" refers to an in-line solution adjustment step in which CCM is combined with a buffer. In a typical buffer exchange step, two solutions (e.g. CCM) and a buffer are mixed or blended together by combining two streams of fluid flowing into a HAPPY device of the invention. For example, a CCM and buffer solution may be required to be combined in order to adjust the pH or osmolality of a CCM prior to entering another HAPPY device that is positioned downstream in the flow path.

As used herein, the term "elute" refers to a process that removes a protein of interest from a chromatography resin by altering the solution conditions such that buffer competes with the molecule of interest for the ligand sites on the chromatography resin. A non-limiting example is to elute a molecule from an ion exchange resin by altering the ionic strength of the buffer surrounding the ion exchange material such that the buffer competes with the molecule for the charged sites on the ion exchange material.

The terms "bind and elute mode" and "bind and elute process," as used interchangeably herein, refer to a product separation technique in which at least one product contained in a sample (e.g., an Fc region containing protein) binds to a chromatographic resin or media and is subsequently eluted.

The terms "contaminant," "impurity," and "debris," as used interchangeably herein, refer to any foreign or objectionable molecule, including a biological macromolecule such as a DNA, an RNA, one or more host cell proteins, endotoxins, lipids and one or more additives that may be present in a sample containing the target product of interest that is being separated from one or more of the foreign or objectionable molecules using a process of the present invention. Additionally, such a contaminant may include any reagent that is used in a step that may occur prior to the purification process.

As used herein, the term "buffer" refers to a solution that resists changes in pH by the action of its acid-base conjugate components. Various buffers that can be employed depending, for example, on the desired pH of the buffer are described in Buffers. A Guide for the Preparation and Use of Buffers in Biological Systems, Gueffroy, D., ed. Calbiochem Corporation (1975).

An "elution buffer" is used to elute the target protein from a chromatography resin. The term "isocratic elution" is used to refer elution condition in which a characteristic of the buffer comprising the mobile phase, for example the pH, ionic strength, or osmolality of the buffer is unchanged during the entire elution process.

The term "gradient elution" is used to refer to elution condition in which a characteristic of the mobile phase is changed or altered in a controlled manner during the elution or recovery of the target biologic product from the substrate.

As used herein the term "perfusion" refers to a cell culture method that is carried out by continuously feeding fresh cell culture medium to a suspension cell culture in a bioreactor and continuously removing cell-free spent medium while retaining the cells in the bioreactor. Typically, perfusion is accomplished via the use of a retention device, such as a hollow-fiber filter. In practice, the size of the pores present in the membrane of the hollow fiber filter will determine whether cells, and/or target protein is returned to the bioreactor. In practice, the cells are continuously filtered from the harvest stream and returned to the bioreactor to maintain a constant culture volume. Cell culture perfusion results in very highly productive bioprocess that can produce higher titers of product than either batch or fed-batch culture methods.

Unless explicitly stated, reference to terms such as "a" or "an" is not limited to one. For example, "a cell" does not exclude "cells." Occasionally phrases such as one or more are used to highlight the possible presence of a plurality. Reference to open-ended terms such as "comprises" allows for additional elements or steps. Occasionally phrases such as "one or more" are used with or without open-ended terms to highlight the possibility of additional elements or steps.

The instant invention provides a harvesting, purification or perfusion yielding (HAPPY) device designed for use external to a bioreactor. Due to the modular nature of the device, it can be assembled in numerous configurations and as a consequence it can be used to perform multiple unit operations required to manufacture a biological product. A common feature of the different embodiments of the HAPPY devices described herein, is the use of a substrate subunit having a porous material covering its top and bottom surface to contain a substrate that is capable of binding a target product. The binding substrate can comprise a chromatography resin but it can be any substrate with an affinity for any target product produced during a production cycle, including a metabolic by-product, component of the culture media, or target protein that is being produced by the host cells. Based on the information disclosed herein, one of skill in the art will immediately recognize that the devices of the invention can be used in numerous combinations, arranged in parallel or in series, to streamline the upstream and downstream unit operations required to produce a target biological product.

The invention also provides methods of using the HAPPY devices of the invention to design robust unit operations for the purpose of achieving high host cell densities and improving product yield, harvesting a target product or purifying a biological product produced during a bioreactor production cycle. In addition to the significant cost savings that are realized from a streamlined manufacturing process that is characterized by the a reduced need for equipment and decreased processing times, the device and methods of the instant invention provide additional savings by using substrate subunits that are designed to facilitate the repeated use of chromatography resins as binding substrates.

More specifically, the invention provides a modular device that allows consolidation of harvesting and purification of target biological products from a CCM. In practice, the invention consolidates three common steps in the manufacturing of target biological products: biological entity removal, volume reduction and capture. The instant invention therefore reduces the cost of manufacturing while also improving the quality of the product.

As described herein, the HAPPY devices of the invention can be assembled using modular components into several alternative configurations. In large part, the number of substrate subunits required to perform a particular unit operation will depend upon a number of considerations including the volume of the bioreactor, the nature of the host cell, the type of substrate that is being used, the binding capacity of the substrate (or substrates that will be present in devices) and the combination of substrate subunits that will be present in the flow path. In order to facilitate the assembly of a high stack of subunits suitable for processing a large volume of cell culture media, the device can be assembled using substrate subunits having housings that include a channel that is dimensioned to receive and accommodate at least a pair of support rods.

Figure 1:
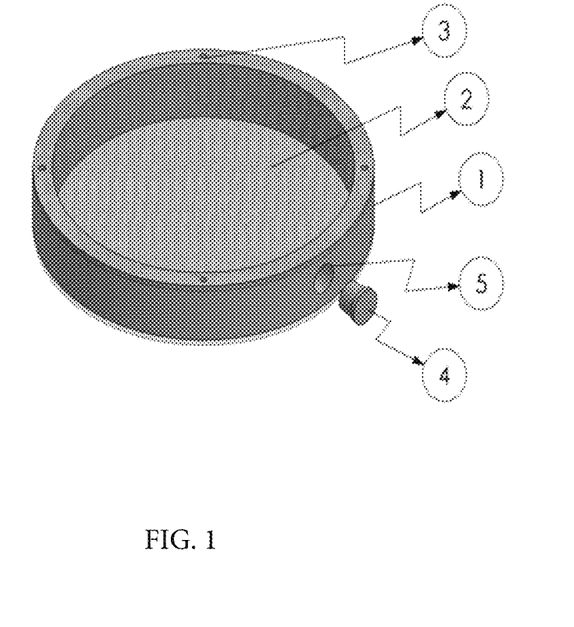
FIG. 1 shows a lateral view of a single substrate subunit.

FIG. 1 shows a lateral view of a single substrate subunit. comprising: a ring-shaped housing (1) defining an interior cavity that is covered on its bottom surface with a porous mesh material or membrane (2); one or two pair(s) of holes (3) dimensioned to accommodate supporting rods that can be optionally used in some embodiments to connect numerous substrate subunits in a stack or column-like configuration; and a plug or stopper (4) dimensioned to fit snuggly into an optional opening (5) in the housing wall to facilitate the introduction of binding substrate into the subunit.

Figure 2:
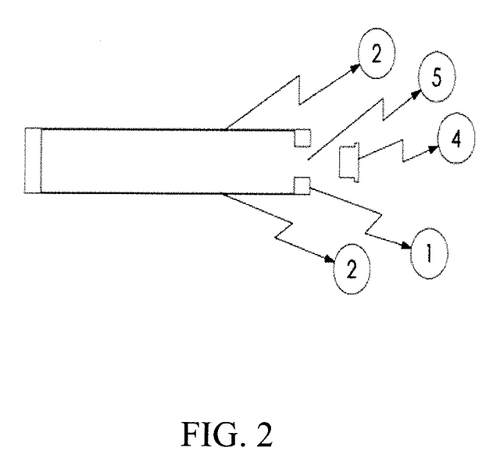
FIG. 2 shows a side view of the substrate subunit illustrating that the top and bottom surfaces of the interior cavity of the subunit are covered with a porous mesh material or membranes.

FIG. 2 shows a side view of the substrate subunit illustrating that the top and bottom surfaces of the interior cavity of the subunit are covered with a porous mesh material or membranes (2), further illustrating how the opening in the housing wall facilitates the introduction of substrate into the interior cavity of the subunit.

Figure 3:
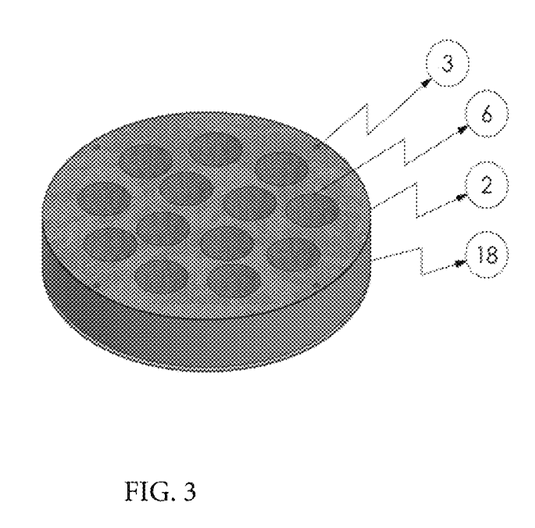
FIG. 3 shows a view of the top (or bottom) surface of a substrate subunit comprising a plurality of channels that define discrete cavities or chambers within the substrate subunit.

FIG. 3 shows a view of the top (or bottom) surface of a substrate subunit having a porous mesh membrane (2) covering the top surface or an alternative housing (18) wherein there is a solid disc-like unit comprising a plurality of channels (6) that define discrete cavities or chambers within the substrate subunit.

Figure 4:
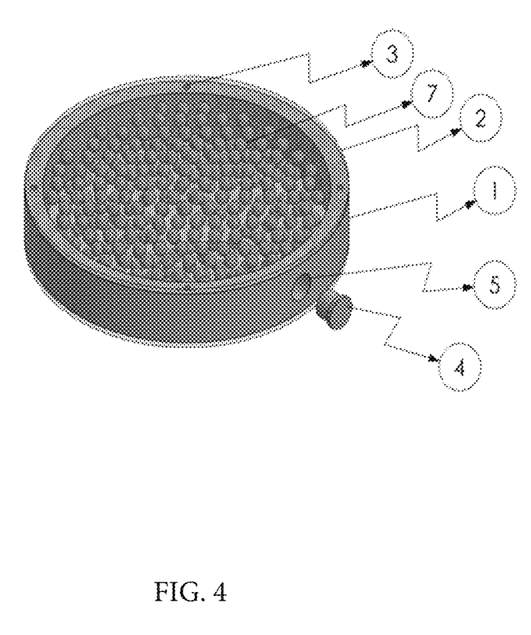
FIG. 4 shows a lateral view of the substrate subunit depicted in FIG. 1 filled with a plurality of substrate beads dispersed on the porous mesh material covering the bottom surface of the subunit.

FIG. 4 shows a lateral view of the substrate subunit depicted in FIG. 1 filled with a plurality of substrate beads (7) dispersed on the porous mesh material covering the bottom surface of the subunit.

Figure 5:
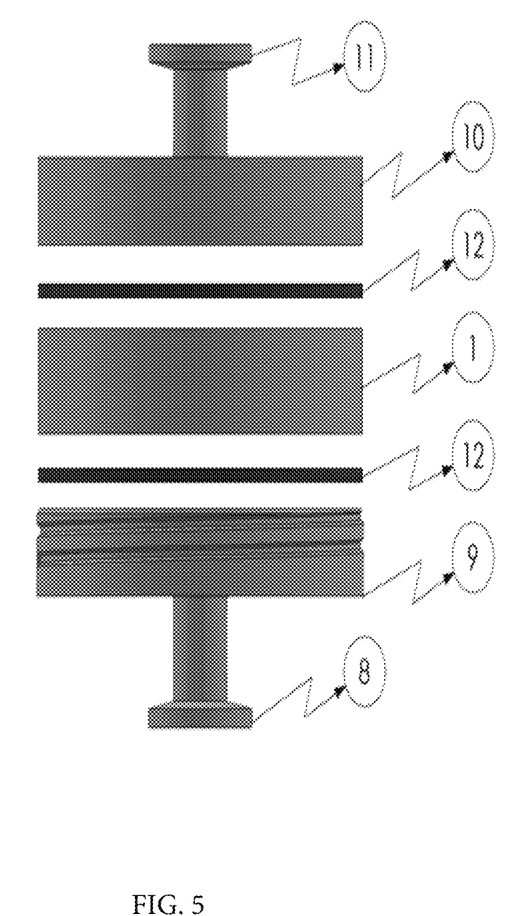
FIG. 5 shows an assembled HAPPY device with a single substrate subunit sandwiched between two gasket rings.

FIG. 5 shows a side view of an assembled HAPPY device that includes a single substrate subunit (1) sandwiched between two gasket rings (12) located between a bottom housing (9) and a top housing (10), wherein the bottom and top housings comprise an inlet (8) and an outlet (11), respectively.

Figure 6:
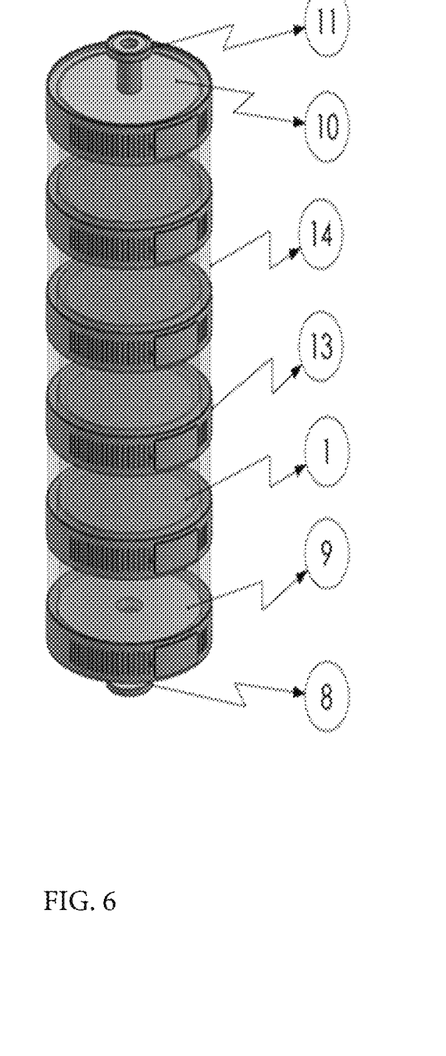
FIG. 6 depicts an alternative HAPPY device assembly that comprises multiple (i.e., six) substrate subunits stacked into a column.

FIG. 6 shows an alternative HAPPY device assembly that comprises multiple (e.g., six) substrate subunits (1) or (18)

stacked into a column contained within a flexible housing (14) disposed between a bottom housing (9) and a top housing (10) wherein each of the substrate subunits is secured to the device by a clamp (13) positioned against the outside surface of the flexible housing and the bottom and top housings include an inlet (8) and an outlet (11).

Figure 7:
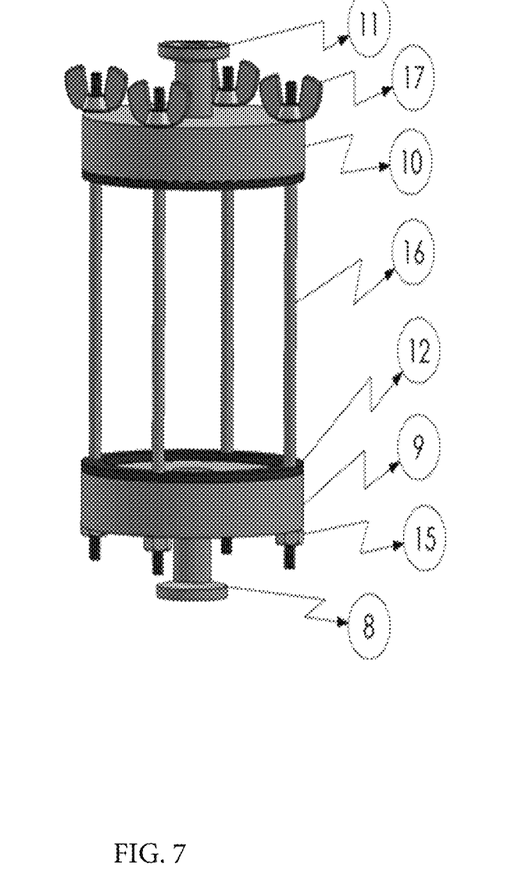
FIG. 7 depicts a housing carousel designed to support an assembled HAPPY device of the invention.

FIG. 7 depicts a housing carousel designed to support an assembled HAPPY device of the invention. The disclosed carousel includes a top housing (10) and a bottom housing (9) adapted to accept supporting rods (16) used to align a number of substrate subunits (not shown, see FIG. 8) using fasteners (15) (depicted as nuts) disposed at the bottom of the vertical supporting rods and a means to tighten or secure the subunits (17) (depicted as wing nuts) disposed at the top of the supporting rods creating a sealed assembly that will accommodate the flow of liquid into and out of the device using the inlet (8) and outlet (11) elements of the top and bottom housing subunits.

Figure 8:
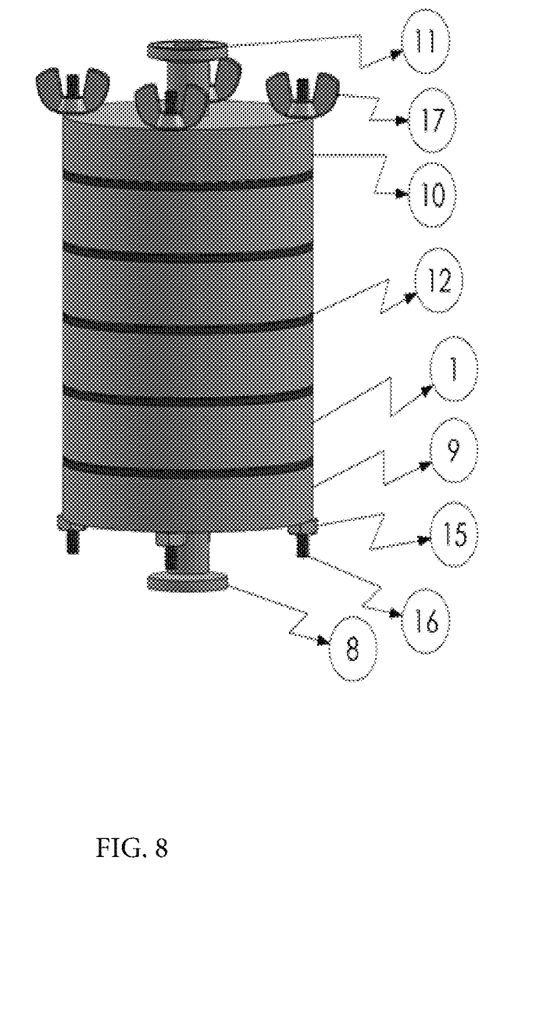
FIG. 8 depicts a HAPPY device of the invention assembled using the carousel depicted in FIG. 7 comprising multiple (e.g., four) substrate subunits or separated by a series of gasket rings stacked together

FIG. 8 depicts a representative HAPPY device of the invention that is assembled on a carousel, such as the one shown in FIG. 7, comprising four support rods. As a point of reference, the carousel depicted in FIG. 7 includes a top housing, and a bottom housing that is adapted to accept supporting rods used to stack and align a number of substrate subunits. The disclosed carousel also includes fasteners (depicted as nuts) disposed at the bottom of the vertical supporting rods and a means to tighten or secure the subunits (depicted as wing nuts) disposed at the top of the supporting rods into a sealed assembly that will accommodate the flow of liquid into and out of the device using the inlet and outlet elements of the top and bottom housing subunits. A suitable carousel for use in the assembly of the HAPPY device of the invention must comprise a means for joining the subunits together into a continuous water-tight stack or column. A person having ordinary skill in the field of chromatography will readily appreciate that alternative fasteners and means of tightening/can be used to assemble the substrate subunits into numerous equivalent assemblies.

In the embodiment depicted in FIG. 8, the device comprises a stack of substrate subunits with gaskets placed between each substrate subunit. The gaskets are an optional feature which a person having ordinary skill in the field of chromatography will readily appreciate could be replaced by an any alternative means of sealing adjoining subunits to achieve a water-tight seal.

Figure 9:
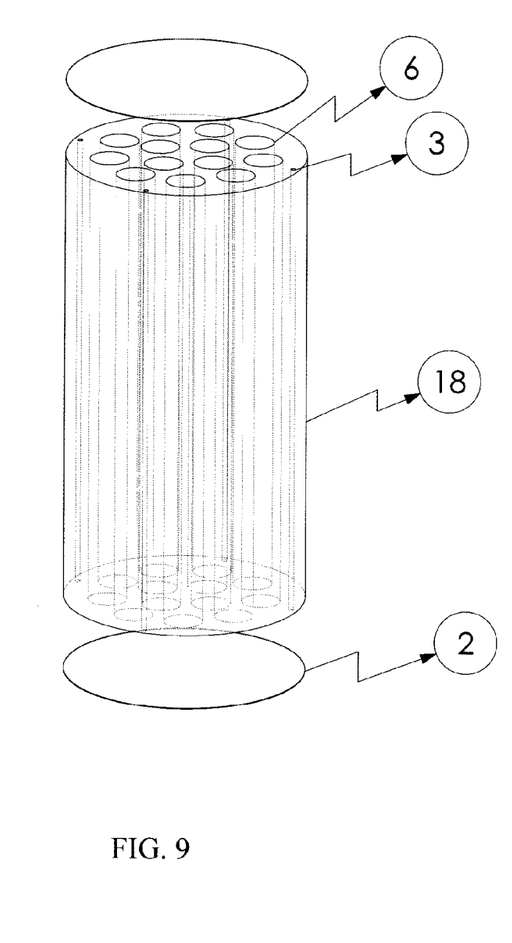
FIG. 9 shows an alternative substrate subunit dimensioned to accommodate long cylinders or tubes of substrate.

FIG. 9 depicts an alternative substrate subunit 3 dimensioned to accommodate long cylinders or tubes of substrate having a porous mesh membrane (2) covering the top surface or an alternative housing (18) that comprises a solid disc-like unit comprising a plurality of channels (6) that define discrete cavities or chambers that can optionally accommodate tubes or cylinders of substrate.

In another alternative embodiment, the HAPPY device of the invention comprises a top and bottom subunit in combination with a single substrate subunit that contains numerous openings sufficient to accommodate a plurality of tubes. The openings open onto the top and bottom surfaces of the substrate subunit and extend the entire length of the substrate subunit. In practice, the "tubes" or containers are held in place in the substrate subunit by the porous mesh material, which is used to seal the top and bottom surfaces of the subunit. This type of substrate subunit accommodates the use of numerous containers having structural features that make it optimal for use in a particular embodiment of the invention. For example, the "tubes" could be glass tubes filled with a resin, or a flexible tube made of mesh material with pores dimensioned to contain a particular substrate. The use of a flexible tube of mesh (that is sealed at each end) to contain a resin, could make the task of sterilizing a resin, or transferring a column of resin having the target bound to it, a more commercially reasonable undertaking. Optimally, the mesh will comprise pores of about 50 µm as most of the resins used have an average diameter size larger than 50 µm. However, one of skill in the art will recognize that in those instances where a finer resin is used, the mesh size of the housing should be reduced accordingly.

As disclosed herein, the housing of the top, bottom and substrate subunits can be made from plastic, glass, metal (e.g. stainless steel or aluminum) or any composite material that is amenable to sterilization by one or more methods. Generally speaking, the housing subunits of the device should be constructed from materials that can be sterilized either by radiation or by autoclaving. Typically, the device housings will be sterilized by gamma radiation. Alternatively, the devices of the invention can be used in a pharmaceutically clean state to avoid contaminating the target product. The importance of how amenable a particular material is to sterilization will vary with the intended use of the device. For example, it will be a particularly important consideration if a HAPPY device is going to be used in a perfusion system where sterility is important; while it will be less important if the device is being used for embodiments wherein the liquid or media removed from the bioreactor is not returned to the bioreactor, or for example, the device is used to remove a metabolic by-product from a bioreactor production system.

In some embodiments, the substrate subunit housing is a ring-like structure which defines a hollow interior cavity that is dimensioned to accommodate a defined volume of binding substrate. It should be noted that although all of the HAPPY devices depicted in the drawings included herein show devices comprising substrate subunits that are circular in shape, the devices can comprise substrate subunits having any alternative shape that is amenable to stacking, and which can accommodate suitable volumes of substrate, such as rectangular or square shaped substrate subunits.

In an alternative embodiment, the substrate subunit is a solid disc-like shape, wherein the disc comprises numerous chambers that are open on the top and bottom surfaces of the subunit and are dimensioned to contain a binding substrate. In yet another alternative embodiment, the substrate subunits used to assemble a HAPPY device of the invention each comprise at least one pair of holes wherein each is dimensioned to accommodate a supporting rod that can be connected to top and bottom housing subunits, and to additional substrate subunits.

The porous mesh material covering the top and bottom surfaces of the individual substrate subunits can similarly be made from any material that is amenable to sterilization. The mesh coverings will typically comprise pores ranging in size from 1 micron to 50 microns and can be permanently attached to the upper and lower surfaces of the substrate subunit housings.

In practice, the binding substrate can be introduced into a modular substrate subunit either by introducing a volume of substrate into a subunit prior to attaching and permanently sealing the mesh material to the top surface of the subunit. Alternatively, a binding substrate can be introduced into the interior of a subunit that already has mesh attached to its top and bottom surfaces using an optional hole or passage present in the wall of the housing.

As disclosed herein, the hole in the housing subunit can be sealed with a plug or stopper. As described herein depending on the nature of the binding substrate, it may be desirable to include a quantity of beads made from glass, or some other inert material, admixed with the binding substrate in any, or all of the substrate subunits used to assemble a HAPPY device of the invention.

In practice, the substrate subunits and binding substrates can either be pre-sterilized separately, or in some instances, it may be possible to sterilize the filled substrate subunit. However, it may be necessary to sterilize the device subunits and the substrate separately, if the conditions required for sterilizing the device are known to be detrimental to the binding substrate. For example, a stainless steel substrate subunit that is covered with a stainless steel mesh material on its top and bottom surface could be pre-sterilized and subsequently loaded with resin that was cleaned by exposure to a high pH solution (e.g. sodium hydroxide). Alternatively, it may be possible to prepare a substrate subunit for use with a cleaning-in-place procedure that is appropriate for both the binding substrate and the subunit material.

For example, if device is being used to facilitate the large scale purification of a therapeutic antibody produced by mammalian cell culture and the substrate subunits comprise a substrate that is a chromatography resin, the substrate may be cleaned between uses with 50 mM sodium hydroxide (NaOH) along with 1M sodium chloride. Benzyl alcohol can also be optionally contacted with the substrate to achieve more effective microbial control.

One of skill in the art of chromatography will readily acknowledge that, depending on the material that the substrate subunit housing is made from, it may be desirable to use sodium hydroxide in combination with an alternative salt, such as sodium sulfate in combination with sodium hydroxide. For example, if the housing or mesh material is made from stainless steel, the use of high concentrations of sodium chloride may promote corrosion of the substrate subunit. It is well within the skill of an investigator having ordinary skill in the field of chromatography to identify the optimal combination of subunit compatibility, cleaning efficiency and substrate/resin stability.

As described herein, the binding substrate can comprise a chromatography resin selected from an affinity resin, an ionic-exchange resin, a hydrophobic resin, a mixed mode resin or a mixture thereof. In particular embodiments, the binding substrate comprises a resin selected from a resin comprising a peptide or protein ligand. The HAPPY device can be used to harvest or capture a target biological product by using a combination of resins placed in a series of HAPPY devices such that dual or multiple affinity processes can be applied simultaneously during or after the completion of the upstream process.

Examples of resins that can be used in the HAPPY device include, but are not limited to, Dual Affinity Polypeptide technology platform, stimuli responsive polymers enabling complexation and manipulation of biological products, mixed mode sorbents, hydrophobic charge induction chromatography, such as MEP, and Q and S HyperCel, Convective Interaction Media from BIA Separations, BioSMB from Tarpon Biosystems, Protein G, single domain camel-derived (camelid) antibodies to IgG, such as CaptureSelect™ from BAC; inorganic ligands, including synthetic dyes, such as Mabsorbent A1P and A2P from Prometic Biosciences, expanded bed adsorption chromatography materials from Upfront Chromatography; ultra-durable zirconia oxide-bound affinity ligand chromatography media from ZirChrom Separations, receptor mimetic ligands, ADSEPT (ADvanced SEParation Technology), peptidic ligands for affinity chromatography, Protein A- and G-coated magnetic beads, fusion biological products with removable portion (tag) having affinity for chromatography media, such as histidine tags, reverse micelles (liposomes), liquid-liquid extraction systems, crystallization, immobilized metal affinity chromatography, hydroxyapatite chromatographic supports, e.g., CHT ceramic type I and type II, Bio-Gel® HT, Bio-Gel® HTP; metal chelating chromatographic resins consisting of an inert resin of immobilized metal ions such as copper, nickel, etc.; as well as non-derivatized silica gels.

Various anionic constituents may be attached to matrices in order to form cationic supports for chromatography. Anionic constituents include carboxymethyl, sulfethyl groups, sulfopropyl groups, phosphate and sulfonate (S). Cellulosic ion exchange resins such as SE52 SE53, SE92, CM32, CM52, CM92, P11, DE23, DE32, DE52, EXPRESS ION S and EXPRESS ION C. Sephadex and Sepharose-based and cross linked ion exchangers are also known under the product names CM Sephadex® C-25, C-50 and SP Sephadex® C-25, SP Sephadex® C-50 and SP-Sepharose®. High Performance, SP-Sepharose®-XL SP-Sepharose®-Fast Flow, CM-Sepharose®-Fast Flow, and CM-Sepharose®-CL-6B, all available from Pharmacia AB.

Examples of ion exchangers for the practice of the invention include but are not limited to, e.g., ion exchangers under the product names MACRO-PREP®, such as for example, Macro-Prep S Support, Macro-Prep High S Support and Macro-Prep CM.

Hydrophobic columns can be used in the purification of the recombinant protein, e.g., in the 2.sup.nd, 3.sup.rd, and/or 4.sup.th purification steps. Hydrophobic interaction chromatography is well known in the art and is predicated on the interaction of hydrophobic portions of the molecule interacting with hydrophobic ligands attached to "chromatographic supports." A hydrophobic ligand coupled to a matrix is variously referred to as an HIC chromatographic support, HIC gel, or HIC column and the like. Examples of HIC include agarose, silica and organic polymer resins, hydrophobic ligands include, but are not limited to, alkyl groups having from about 2 to about 10 carbon atoms, such as butyl, propyl, or octyl, or aryl groups such as phenyl.

One of the most common resin used to capture therapeutic antibody products is Protein A, which currently costs around $20,000 per liter. The handling of resin that is required to clean and recycle Protein A that is used in traditional downstream unit operations (using standard chromatography columns) invariably results in a significant loss reducing the total value of the resin. In contrast, the modular design of the substrate subunits that are used in the HAPPY devices of the invention minimizes the loss of resin during cleaning and recycling manipulations. The loss of resin is minimized due to the reduced level of manipulation that is required to clean and recycle the chromatography resins which are sealed within a substrate subunit that is covered by a porous membrane which makes the resin more amenable to cleaning and recycling with fewer required manipulations.

In one embodiment, the HAPPY device of the invention comprises more than one substrate subunit, wherein each of the subunits comprise the same binding substrate. In another subunit, the HAPPY device of the invention comprises more than one substrate subunit and some of the subunits present in the device comprise a different substrate than at least one other substrate subunit present in the device. While each subunit can comprise a single binding substrate, a plurality of substrates can be placed inside each subunit or a plurality of subunits can be used in the device, each subunit containing a different binding substrate that have the ability to bind a variety of target biological products.

The HAPPY devices of the invention can be used in a flow path that is part of a closed-loop system to harvest a target biological product produced by host cells in a bioreactor. The target biological product will generally be recombinant expressed proteins or antibodies but these could well be any biological product, a metabolite, an impurity or any chemical in the culture media that needs to be separated from the conditioned culture media (CCM).

In general terms, the HAPPY device of the invention can be used to harvest a target biological product from a cell culture media (CCM) by: a) creating a flow-path between a source of cell culture media from a bioreactor and the inlet port of a HAPPY device comprising a binding substrate thereby creating a flow path using pre-sterilized tubing; b) forcing the CCM into the flow path and through the substrate subunits of the device either under gravity or by action of a pump; c) maintaining the CCM under conditions most optimal for binding of the target biological product to the binding substrate contained within the substrate subunit, thereby producing a product-depleted culture media; and optionally d) collecting the product-depleted CCM flowing out of the outlet port of the device and returning it to the bioreactor or discarding it.

In practice the binding substrate can either specifically bind or non-specifically absorb a component of the culture media or product of the production cycle, including cellular debris or host cell protein. Suitable binding substrates include but are not limited to Ni-NTA His•Bind® resin, affinity resin, ion exchange resin, heparin affinity resin, and chelating resin. For example, if the target biological protein of interest is an antibody or an Fc-containing protein, such as a fusion protein, appropriate binding resins would include Protein A and Protein G.

Typically, the product will be harvested at the end of a manufacturing process. However, in an alternative embodiment a HAPPY device of the invention could be used either intermittently (e.g. periodically) during a production cycle to remove an expressed target biological product from the spent media collected from a bioreactor or continuously throughout the production cycle.

For example, a device of the invention comprising an affinity media could be used to harvest or capture a biological product at a preset point during the production cycle (e.g. based on product titer, or cell density, or another suitable process control trigger point. The product-depleted CCM that is collected from a HAPPY device comprising a suitable resin for harvesting the target biological product can be removed from the flow-path, and the harvested biological product can be eluted and further processed outside the bioreactor using downstream unit operations. Alternatively, the eluted product can be further purified (e.g. polished) by directing it through an additional series of HAPPY devices comprising appropriate substrates.

In practice, it may be desirable to introduce a porous filter having a pore size that will prevent cells from entering into the HAPPY harvesting device into the flow path between the bioreactor and the HAPPY device. For example, a hollow fiber filter designed for use in a perfusion culture system having a large pore membrane (i.e. >0.1 uM) which will allow expressed proteins but not cells to pass through.

Alternatively, any other non-clogging filter comprising a porous membrane that will retain the cells can be used to prevent entry of host cells into the harvesting device. As disclosed herein, it may also be desirable to include another HAPPY device comprises substrate subunits with a binding substrate selected for its ability to remove process-related contaminants such as host cell proteins, cellular debris and deleterious metabolic by-products from the CCM into the flow-processing path prior to the HAPPY device comprising the binding substrate.

The binding rate of the target biological product and the binding substrate can generally be increased if the temperature of the culture media is lowered and this can be accomplished by passing the culture media through a heat exchanger prior to its entry into the HAPPY device. Alternately, ideal binding temperatures can be determined and the conditions of binding optimized by adjusting the temperature either of the culture media or the entire HAPPY device assembly.

In practice, a plurality of HAPPY devices can be used in combination to capture a target biological product by using more than one binding substrate placed in a series of devices such that dual, or multiple affinity processes, can be simultaneously exploited to capture the target biological product either during or upon completion of a production cycle.

As disclosed herein, a HAPPY device of the invention can also be assembled using substrate subunits that are packed with various chromatography resins and used to accomplish downstream unit operations. When used in this context, all of the substrate subunits present in a single device can comprise a single type of binding substrate, and limitations based on the binding capacities of the volume of resin that can be accommodated in a single device can be addressed by using a plurality of devices connected in a single flow path.

One of skill in the art will readily acknowledge that in an alternative embodiment, a plurality of devices aligned in a single path could also be used to perform multiple downstream purification functions including capturing/harvesting of the expressed target protein of interest as well as purification and/or polishing.

Depending upon the nature of the target protein, it may be advantageous to either perform the harvesting or purification steps in a cold room or to use a cooling condenser to cool the CCM prior to passing it through the HAPPY device of the invention.

For example, it may be desirable to cool the cell culture media to a temperature between 0° C. and 25° C. If the method is being used to harvest a drug product from the CCM, then it is contemplated that more than one and possibly several, HAPPY devices may be used in combination to capture and purify the target protein. For example, the flow path could include sets of HAPPY devices arranged in a predetermined series, or in parallel to accomplish the downstream purification steps required to isolate a drug product.

In practice, the final drug product can be eluted from a polishing chromatography resin that is operated in bind and elute mode by introducing, through one of the ports, at least one elution buffer capable of disrupting a binding interaction between the target biological protein and the substrate. Depending upon the nature of the chromatography resin and the sequence of the purification steps that is employed, the elution step may include a buffer exchange step to adjust the pH, ionic strength or osmolality of the resulting eluate and the elution step be accomplished using either an isocratic or gradient elution.

Typically, a perfusion process is done by removing spent media through a filter (e.g., a hollow-fiber filter) which functions to recirculate host cells back into the bioreactor (e.g. the retentate). Perfusion mode provides a constant environment favorable to the cells by continuous by-product removal and nutrient addition. In comparison to batch and fed-batch modes, the perfusion mode allows prolonging healthy cultures, potentially at high cell density, as well as a short residence time of the product in the bioreactor.

However, this approach creates significant contamination and yield issues because the filtration process stresses the host cells, which can in turn elaborate host cell proteins, including proteases which are known to have an adverse effect on the stability and quality of the harvested protein. The instant invention offers an alternative approach by creating a closed loop perfusion system which includes a HAPPY device of the invention downstream of a hollow-fiber filter, such that the spent media is continuously or intermittently directed through one or more HAPPY devices for the purpose of capturing the target product from the CCM as soon as it is produced.

Alternatively, a target product-depleted host cell culture fluid can be removed periodically from the system by directing the flow into a separate collection vessel that is outside of the flow path. HAPPY devices can be attached and removed from the flow path of the culture media to provide continuous capture while the host cells are redirected to, or retained within the bioreactor. Further, the HAPPY devices of the invention can be used to bind and remove undesirable culture by-products and metabolites that can accumulate during host cell culture by connecting in series additional HAPPY devices that may contain adsorbents specific to the metabolites. Since the culture media is returned to the bioreactor, the cost of new media is also obviated.

What is claimed is:

1. A reusable, gravity-driven, target product capture device comprising:
    a top housing subunit with a liquid inlet, a bottom housing subunit with a liquid outlet, both housing subunits further defined by an interior cavity and a housing wall;
    at least one substrate subunit having a top and bottom surface, disposed between the top and bottom housing subunits, defined by an interior cavity and a housing wall extending from the top to the bottom surface; the interior cavity of the substrate subunit comprising a plurality of inert beads admixed with and a volume of a resin binding substrate capable of binding the target product; the top and bottom surfaces further comprising a porous mesh material having pore size smaller than the size of the granular binding substrate; and an opening in the housing wall of the substrate subunit, provided with a plug, to introduce and hold a binding substrate in the substrate subunit;
    a sealing gasket disposed between each subunit;
    a means of tightly holding the subunits in a vertical arrangement comprising:
    at least one pair of vertical holes in the housing walls of subunits and the gaskets dimensioned to accommodate a wing-nut bolt passing through the subunits; or,
    a flexible tubular housing defining, an interior cavity dimensioned to contain the subunits snugly to prevent liquid from flowing between the subunits.

2. The device of claim 1, wherein the subunits are comprised of plastic, glass, metal or a composite material and the porous mesh, material is comprised of plastic, metal or a composite material.

3. The device of claim 1, wherein the substrate subunit is divided into a plurality of compartments, with or without the beads.

4. The device of claim 1, wherein a plurality of substrate subunits comprises a different binding substrate.

5. The device of claim 1, wherein the target product comprises:
    therapeutic proteins produced by recombinant host cells including as an example, a bacterium, yeast, hybridoma, baculovirus, mammalian cell or plant cell and the binding substrate used to capture therapeutic proteins, as an example, a resin selected from an affinity resin, an ionic-exchange resin, a cation exchange resin, a hydrophobic resin, a mixed mode resin, a peptide ligand, a protein ligand and a mixture thereof;
    metabolic by-product of the recombinant host cell including as an example, acetate, carbon dioxide, endotoxins, ethanol, lactic acid, citric acid glutamic acid, lysine, threonine, tryptophan and other amino acids, antibiotics, antiseptics, bacteriocins, and fungicides and the binding substrate used to capture metabolic by-product, as an example, solid granular substances capable of specifically binding one or more by-product;
    cellular debris or host cell protein capture by using the binding substrate, as an example, Ni-NTA His binding resin, affinity resin, Protein A resin, Ion exchange resin, heparin affinity resin, a chelating resin, or a mixture thereof.

* * * * *